United States Patent [19]

Ancillotti et al.

[11] 4,039,590
[45] Aug. 2, 1977

[54] PROCESS FOR THE SYNTHESIS OF METHYL-TERT-BUTYL ETHER FROM METHANOL AND ISOBUTYLENE IN THE PRESENCE OF BUTADIENE

[75] Inventors: Francesco Ancillotti, San Donato Milanese; Ermanno Pescarollo, Milan; Marcello Massi Mauri, San Donato Milanese, all of Italy

[73] Assignee: Snam Progetti S.p.A., Milan, Italy

[21] Appl. No.: 579,662

[22] Filed: May 21, 1975

[30] Foreign Application Priority Data

May 21, 1974 Italy .................................. 23010/74

[51] Int. Cl.$^2$ ........................ C07C 41/06; C07C 41/10
[52] U.S. Cl. ........................... 260/614 A; 260/681.5 R
[58] Field of Search ............. 260/614 A, 614 R, 681.5

[56] References Cited

U.S. PATENT DOCUMENTS

| | | | |
|---|---|---|---|
| 2,391,084 | 12/1945 | Carmody | 260/614 A |
| 2,480,940 | 9/1949 | Leum et al. | 260/614 A |
| 3,846,088 | 11/1974 | Brown et al. | 260/614 A X |

FOREIGN PATENT DOCUMENTS

| | | | |
|---|---|---|---|
| 2,011,826 | 10/1970 | Germany | 260/614 A |
| 877,818 | 0000 | Italy | 260/614 A |
| 957,000 | 4/1964 | United Kingdom | 260/614 A |
| 1,176,620 | 1/1970 | United Kingdom | 260/614 A |

*Primary Examiner*—Howard T. Mars
*Attorney, Agent, or Firm*—Ralph M. Watson

[57] ABSTRACT

Isobutylene is separated from a stream of $C_4$ hydrocarbons containing it and remarkable amounts of butadiene, and methyl tert-butyl ether is prepared, by feeding that stream of hydrocarbons and methanol to a reactor containing a catalyst consisting of an acid ion-exchange resin, maintained at a temperature in the range of from 60° to 120° C, at a space velocity (LHSV) in the range of from 5 to 35, the relation between the space velocity (LHSV) and temperature being correlated to correspond to the formula: LHSV = $\frac{1}{2}$t - 25, wherein t is the temperature in degrees C, so that the isobutylene and methanol are caused to react, and then separating the methyl tert-butyl ether thus formed from the reaction mixture by distillation.

2 Claims, No Drawings

PROCESS FOR THE SYNTHESIS OF METHYL-TERT-BUTYL ETHER FROM METHANOL AND ISOBUTYLENE IN THE PRESENCE OF BUTADIENE

The present invention relates to a process for the synthesis of alkyl ter-butyl ethers starting from a primary alcohol and isobutylene in the presence of butadiene.

More particularly, the present invention relates to a process for the synthesis of methyl tert-butyl ether from methanol and isobutylene in the presence of butadiene.

In the following description, reference will be made exclusively to the synthesis of methyl tert-butyl ether even though the process is obviously suitable to the preparation of other alkyl tert-butyl ethers from other primary alcohols.

It is known that methanol can be reacted with isobutylene so producing methyl-tert-butyl ether (EMTB).

The reaction is catalyzed by mineral acids (for instance sulphuric acid), organic salts (sulphonic acid) and ion-exchange resins; particularly suitable for this purpose are the sulphonated styrene-divinyl benzene copolymers.

The reaction of addition of methanol is selective for isobutylene and other olefines having a tertiary carbon atom with a double bond, while under the same operating conditions the linear olefins such as butene 1 and butene 2 (cis and trans) prove to be inert; the aforesaid selectivity makes it possible to use for the synthesis of EMTB isobutylene contained in commercial cuts such as, for instance, the $C_4$ olefinic fraction coming from catalytic cracking.

It is known that the sulphonated styrene-divinyl benzene resins, used as catalysts for the synthesis of EMTB, also catalyze the dimerization and polymerization of dienes; consequently, when one wants to use, for the synthesis EMTB, in olefinic cuts rich of butadiene, for instance the $C_4$ fraction coming from steam cracking, the diene should be previously extracted or selectively hydrogenated (British Pat. No. 957,000). A confirmation of this can be found in the prior patent literature wherein in all quoted examples butadiene is absent or is not more than 2-4% (see Italian Patent 877,818; French Pat. No. 1,256,388 and German OS 2,011,826)

It is obvious that this limits the use of fractions coming from steam cracking and that neither of the suggested solutions, previous extraction of butadiene or its prehydrogenation, prove to be very practical, since the first solution requires the EMTB synthesis plant to be downstream of the butadiene extraction plant and the second solution involves the loss of a valuable hydrocarbon.

It has been found that under suitable working conditions the isobutylene etherification can be carried out in the presence of remarkable amounts of butadiene, limiting the losses of the same to values lower than 2%. The losses are substantially due to the formation of butenyl ethers, dimers and codimers.

The subject of the present invention is a process for the synthesis of alkyltert-butyl ethers from a primary alcohol and isobutylene in the presence of butadiene consisting in feeding a $C_4$ hydrocarbon stream containing isobutylene and butadiene together with the primary alcohol to a synthesis zone containing, as catalyst, an ion-exchange resin in acid form, at a temperature in the range of from 60° to 120° C, preferably between 60° and 80° C, with a space velocity (LHSV) in the range of from 5 to 35 and in separating the obtained ether from the other compounds by distillation.

Preferably the space velocity is bound to temperature by the relation:

$$LHSV = \tfrac{1}{2} t - 25$$

wherein LHSV is the space velocity expressed in volume of liquid per hour and per volume of catalyst and t is the temperature expressed in ° C.

In the particular case of the synthesis of methyltert-butyl ether the aforesaid conditions remain unchanged and obviously the alcohol is methyl alcohol.

A further aspect of the present invention is a process for separating isobutylene from a $C_4$ hydrocarbon stream containing butadiene by etherification of isobutylene in the aforesaid manner with a primary alcohol and subsequent separation of the produced ether by distillation.

The possibility of carrying out the EMTB synthesis from butadiene rich streams solves the problems discussed above and moreover offers the opportunity to have, as side product, an olefinic cut, further enriched in butadiene, with a consequent advantage when such diene has to be possibly recovered.

The selective etherification of isobutylene in the presence of remarkable amounts of butadiene is possible as we have found working conditions which make it possible to control kinetically the secondary butadiene reactions; under conditions different from those found by us the butadiene losses can reach 20%-30%.

We shall now give some examples with the aim of better illustrating the invention without limiting it in any way.

EXAMPLE 1

130 grams of a $C_4$ olefinic cut coming from steam cracking and having the following percent composition:

| | |
|---|---|
| propylene % by weight | 6.03 |
| propane | absent |
| isobutane | 0.86 |
| n-butane % by weight | 3.73 |
| butene 1 | 16.44 |
| isobutylene | 29.19 |
| butene 2 trans | 5.89 |
| butene 2 cis | 4.29 |
| 1.3 butadiene | 39.57 | were introduced into an autoclave together with 20 grams of methanol (isobutylene/methanol molar ratio = 1.03) and 12 grams of Amberlyst 15, used as catalyst.

The above $C_4$ feedstock contains 1,3-butadiene as a major constituent.

The mixture was reacted at 80° C under strong stirring.

During the reaction samples were withdrawn which were analyzed with the following results:

| time minutes | 15 | 30 | 60 | 120 | 150 |
|---|---|---|---|---|---|
| Isobutylene conversion (% by weight) | 66.53 | 75.01 | 79.82 | 75.10 | 71.54 |
| Methanol conversion (% by weight) | 68.47 | 77.62 | 87.69 | 92.26 | 93.25 |
| Butadiene conversion (% by weight) | <0.1 | <0.1 | 1.2 | 4.66 | 8.76 |
| Linear butenes conversion | | | | | |

-continued

| time minutes | 15 | 30 | 60 | 120 | 150 |
|---|---|---|---|---|---|
| (% by weight) | <0.1 | <0.1 | <0.1 | <0.1 | <0.1 |

The losses of butadiene were due to the formation of methyl butenyl ethers with minor amounts of dimers (vinylcyclohexene) and codimers. As shown in example 1, carried out discontinuously, an excessive residence time not only reduces the butadiene recovery but also negatively influences the conversion of isobutylene; under the conditions of the example the conversion of isobutylene reached a maximum after 60 minutes and afterwards it decreased.

This behaviour is due to the fact that EMTB, methanol and isobutylene reach in short times the thermodynamic equilibrium and afterwards while methanol is consumed for producing products of addition to butadiene (butenyl ethers) the system reacts by decomposing again EMTB in its constituents so restoring the equilibrium.

EXAMPLES 2, 3 and 4

The olefinic cut described in example 1 was continuously reacted with methanol in the presence of Amberlyst 15 in a plug flow reactor. The working conditions and the obtained conversions are reported in the following table.

| Examples | 2 | 3 | 4 |
|---|---|---|---|
| temperature (° C) | 60 | 80 | 80 |
| LHSV | 5 | 5 | 15 |
| Molar ratio isobutylene/methanol | 1 | 1 | 1 |
| Isobutylene conversion (%) | 77.6 | 70.7 | 79.1 |
| Butadiene conversion | 1.3 | 11.5 | 1.8 |
| Linear butenes conversion | <0.1 | <0.1 | <0.1 |

Considerations analogous to the ones of example 1 are obtainable from the tests of examples 2, 3, 4 carried out continuously in a plug flow reactor (continuous reactor with plug flow). Therefore we have found that once the temperature has been selected there is an optimum space velocity LHSV; higher values involve higher butadiene recoveries but isobutylene conversions lower than the equilibrium value, LHSV lower than the optimum value involve secondary reactions of butadiene and lower conversions of isobutylene.

What we claim is:

1. In a process of synthesizing methyl tert-butyl ether by reacting methanol with isobutylene in the presence of butadiene, wherein the improvement comprises feeding a stream of methanol and C-4 hydrocarbons containing butadiene as a major constituent and isobutylene to a reactor containing a catalyst consisting of an acid ion-exchange resin in the temperature range of from 60° to 120° C and at a space velocity (LHSV) in the range of from 5 to 35, and correlating said space velocity (LHSV) and temperature so that they correspond to the formula: $LHSV = \frac{1}{2} t - 25$, wherein t is the temperature in degrees C, whereby said methanol and isobutylene are caused to react to form methyl tert-butyl ether, and then separating said methyl tert-butyl ether from the reaction mixture by distillation.

2. The process of separating isobutylene from a stream of C-4 hydrocarbons containing butadiene as a major constituent and said isobutylene, which consists in feeding said stream and methanol, at a space velocity (LHSV) in the range of from 5 to 35, to a reactor containing a catalyst consisting of an acid ion-exchange resin, in the temperature range of from 60° to 120° C, and correlating said space velocity (LHSV) and temperature so that they correspond to the formula: $LHSV = \frac{1}{2} t - 25$, wherein t is the temperature in degrees C, whereby said isobutylene and methanol are caused to react to form methyl tert-butyl ether, separating said methyl tert-butyl ether from the reaction mixture by distillation, and recovering an isobutylene-free stream of hydrocarbons containing said butadiene.

* * * * *